United States Patent
Hurley et al.

(10) Patent No.: US 12,036,295 B2
(45) Date of Patent: Jul. 16, 2024

(54) MOIST WIPE HAVING ENHANCED DISPERSIBILITY

(71) Applicants: Nice-Pak Products, Inc., Orangeburg, NY (US); Haso Ltd., Tokyo (JP)

(72) Inventors: Jeffrey Scott Hurley, Ardsley, NY (US); Alan Joseph Suares, Upper Saddle River, NJ (US); John Matthew Iarocci, Rye Brook, NY (US); Nilgun Auriemma, Rockaway, NJ (US); Arthur Ray Love, Nutley, NJ (US); Kelly Maureen Kurtz, Stony Point, NY (US); Kikuo Yamada, Tokyo (JP)

(73) Assignees: Nice-Pak Products, Inc., Orangeburg, NY (US); Haso Ltd., Tokyo (JP)

( * ) Notice: Subject to any disclaimer, the term of this patent is extended or adjusted under 35 U.S.C. 154(b) by 701 days.

(21) Appl. No.: 17/274,840

(22) PCT Filed: Sep. 12, 2019

(86) PCT No.: PCT/US2019/050826
§ 371 (c)(1),
(2) Date: Mar. 10, 2021

(87) PCT Pub. No.: WO2020/056146
PCT Pub. Date: Mar. 19, 2020

(65) Prior Publication Data
US 2022/0047468 A1    Feb. 17, 2022

Related U.S. Application Data

(60) Provisional application No. 62/730,054, filed on Sep. 12, 2018.

(51) Int. Cl.
| | |
|---|---|
| *A61K 8/02* | (2006.01) |
| *A61K 8/20* | (2006.01) |
| *A61K 8/34* | (2006.01) |
| *A61K 8/73* | (2006.01) |
| *A61K 8/86* | (2006.01) |
| *A61Q 19/00* | (2006.01) |
| *A61Q 19/10* | (2006.01) |
| *D21H 11/02* | (2006.01) |
| *D21H 13/08* | (2006.01) |
| *D21H 17/27* | (2006.01) |
| *D21H 27/00* | (2006.01) |

(52) U.S. Cl.
CPC ............ *A61K 8/0208* (2013.01); *A61K 8/027* (2013.01); *D21H 11/02* (2013.01); *D21H 17/27* (2013.01); *D21H 27/005* (2013.01); *D21H 13/08* (2013.01)

(58) Field of Classification Search
CPC .......... A61B 17/11; A61B 2017/00004; A61B 2017/00893; A61B 2017/1107; A61B 2017/1132; A61F 2/0077; A61F 2/064; A61F 2/07; A61F 2002/009; A61F 2210/0004; A61F 2220/0016; A61F 2250/0067; A61K 8/0208; A61K 8/027; A61K 8/20; A61K 8/345; A61K 8/731; A61K 8/86; A61M 2037/0046; A61M 37/0015; A61Q 19/10; A61Q 19/00; D21H 11/02; D21H 13/08; D21H 17/27; D21H 27/005

See application file for complete search history.

(56) References Cited

U.S. PATENT DOCUMENTS

| | | |
|---|---|---|
| 6,338,855 B1 | 1/2002 | Albacarys et al. |
| 2011/0293931 A1 | 12/2011 | Vogel et al. |
| 2015/0150792 A1 | 6/2015 | Klingman |
| 2018/0140529 A1 | 5/2018 | Miller, IV et al. |

FOREIGN PATENT DOCUMENTS

| | | |
|---|---|---|
| JP | 1990-149237 A | 6/1990 |
| JP | 1999-508611 A | 7/1999 |
| JP | 2002-509463 A | 3/2002 |
| WO | 9740815 A1 | 11/1997 |
| WO | 9901536 A1 | 1/1999 |

OTHER PUBLICATIONS

Machine translation of Office Action in corresponding Mexico Application No. MX/a/2021/002956, mailed Jul. 6, 2023, 12 pages.
Office Action in corresponding Chinese Application No. 201980067630.1, mailed Mar. 7, 2023, 16 pages.
European Search Report in EP Application No. 19859623.1-1109/3849497, mailed Jul. 19, 2022 (10 pages).
Office Action in corresponding Chinese Application No. 201980067630.1, mailed Oct. 20, 2021, 25 pages.
Machine translation of Office Action in corresponding Japanese Application No. 2021-513794, mailed Aug. 18, 2023, 31 pages.
Machine translation of Office Action in corresponding Mexico Application No. MX/a/2021/002956, mailed Nov. 8, 2023, 10 pages.
Machine translation of Office Action in corresponding Japanese Application No. 2021-513794, mailed Jan. 9, 2024, 6 pages.

*Primary Examiner* — Jeffrey T. Palenik
(74) *Attorney, Agent, or Firm* — Leason Ellis LLP

(57) ABSTRACT

Moist wipes having improved dispersibility are provided. The moist wipes are sufficiently strong during use and disperse sufficiently quickly under real world conditions to be flushable without creating potential problems for sanitation systems.

18 Claims, 4 Drawing Sheets

MOIST WIPE HAVING ENHANCED DISPERSIBILITY

CROSS-REFERENCE TO RELATED PATENT APPLICATIONS

This application is a U.S. National Phase Application under 35 U.S.C. § 371 of International Patent Application No. PCT/US2019/050826, filed Sep. 12, 2019, which claims the priority of U.S. Provisional Patent Application 62/730,054, filed Sep. 12, 2018, which is incorporated by reference as if expressly set forth in its entirety herein.

FIELD OF THE INVENTION

The present invention relates to wipes having improved dispersibility compared to existing dispersible wipes, including moist toilet tissue, cleaning, sanitizing and disinfecting wipes, and personal care wipes. The wipes are sufficiently strong for use and have improved dispersibility compared to existing products.

BACKGROUND OF THE INVENTION

Many wipe products not designed to be flushed are being flushed, including baby, surface, and personal hygiene wipes. Certain categories of wipes are suitable for flushing after they are used. It is desirable for such flushable wipes to breakdown relatively quickly and disperse in municipal sanitization systems. At the same time, a dispersible wipe should not breakdown so quickly as to fail during its proposed use.

Some known wipes marketed as flushable require a relatively long period of time and/or agitation and/or thermal energy within water for their post-use strength to decrease sufficiently to allow them to disperse.

Currently marketed flushable wipe products include a non-woven component comprised of short cellulose fibers (pulp) and long cellulose fibers. Other products may use a salt trigger binder that is comprised of short and medium length cellulose fibers, a binder system comprised of one or more components and a liquid that maintains the strength of the wipe due to a salt concentration that is higher than what is present in a typical municipal waste water system. Fibers may bound together through chemical and/or mechanical processes. Following use, these products may be flushed because they are designed to disentangle and disperse in the course of going through plumbing where they are introduced to agitation and high water volume.

The ideal flushable wipe would have sufficient comfort and strength to be used for its intended purpose, and very rapid dispersion upon being flushed. The more rapidly such wipe disperses, the less likely potential problems such as downstream clogging will occur. Thus, the technical challenge is to produce a wipe that has the seemingly conflicting properties of strength for use and rapid dispersibility after use.

Thus, there is a need to provide an improved dispersible wipe that (i) is sufficiently strong during use and (ii) disperses quickly (under real world conditions) to avoid problems for sanitation systems.

SUMMARY OF THE INVENTION

The present invention relates to a moist wipe having both improved dispersibility and sufficient strength to be used as, among other things, moist toilet issue, cleaning, sanitizing, and disinfecting wipes, and/or other personal care wipes. The present invention is a significant advancement over current technology because it provides, e.g., a moist wipe, comprised of a homogeneous fibrous material (e.g., non-woven) component that is not hydroentangled and a liquid component, that disperses more quickly than currently marketed products. Surprisingly, a moist toilet tissue of the present invention disperses even more quickly than conventional toilet tissue.

The present invention is technologically distinguished and advanced relative to existing dispersible wipe products for several reasons. A homogeneous fibrous material (e.g., non-woven) component of the present invention is not formed by hydroentanglement, and its dispersement does not rely on the disentanglement of fibers. A moist wipe of the present invention disperses more rapidly than existing products that include a hydroentangled non-woven component.

The present inventors have met the challenge of achieving a more rapidly dispersible wipe, which still provides sufficient safety, comfort, and strength, by combining the non-woven, non-hydroentangled homogeneous fibrous component with a novel liquid component.

Furthermore, by experimentation, the present inventors have identified certain liquid components for the presently claimed products that provide one or more of the following additional beneficial features: i) improved aesthetic features, such as improved feel to the skin (less greasy and/or tacky), ii) improved settling properties, iii) improved odor control, iv) improved preservative qualities, v) enhanced pH stability, vi) lower toxicity and vii) lower production costs.

In one aspect, the present invention relates to a moist wipe comprising:
 a. a homogeneous fibrous material (e.g., a non-woven material) comprising one or more water soluble binders; and
 b. a liquid component comprising
   i. about 65 to about 90% w/w (e.g., about 65 to about 75% w/w or about 70 to about 75% w/w) of water,
   ii. about 10 to about 35% w/w (e.g., about 10 to about 25% w/w or about 15 to about 20% w/w) of an organic solvent, and
   iii. about 1 to about 10% w/w (e.g., about 3 to about 5% w/w) of a multivalent (e.g., divalent) salt.

In another aspect, the present invention relates to a moist wipe comprising:
 a. a homogeneous fibrous material (e.g., a non-woven material) comprising one or more water soluble binders and
 b. a liquid component comprising
   i. about 0% to about 80% w/w (e.g., about 10 to about 60% w/w or about 25 to about 35% w/w) of water,
   ii. about 20 to about 100% w/w (e.g., about 10 to about 25% w/w or about 15 to about 20% w/w) of an organic solvent, and
   iii. optionally, about 0 to about 10% w/w (e.g., about 3 to about 5% w/w) of a multivalent (e.g., divalent) salt.

In embodiments of the invention, the homogeneous fibrous material comprises wood pulp and carboxymethyl cellulose (CMC).

The multivalent salt may be an inorganic or an organic multivalent salt. In one embodiment, the multivalent salt is a divalent salt. Suitable examples of multivalent salts include, but are not limited to, salts of the alkaline earth metals and the transitions metals. Suitable divalent cations include, but are not limited to, $Zn^{2+}$, $Be^{2+}$, $Mg^{2+}$ and $Ca^{2+}$, and any combination thereof. Suitable anions include, but are not limited to, halides (fluoride, chloride, bromide, iodide), sulphates, sulphites, thiosulfates, carbonates, oxides, nitrates, nitrites, phosphates, hydrogen phosphates, and the like. For example, the multivalent salt may be, but is not limited to, $ZnF_2$, $ZnCl_2$, $ZnBr_2$, $ZnI_2$, $MgF_2$, $MgCl_2$, $MgBr_2$, $MgI_2$, $BeF_2$, $BeCl_2$, $BeBr_2$, $BeI_2$, $CaF_2$, $CaCl_2$, $CaBr_2$, $CaI_2$, $ZnSO_4$, $ZnSO_3$, $BeSO_4$, $BeSO_3$, $MgSO_4$, $MgSO_3$, $CaSO_4$, $CaSO_3$, ZnO, MgO, CaO, BeO, and any combination thereof.

In one embodiment, the organic solvent may be an alcohol, such as a polyol, or a polyol ether. In an aspect of the invention, the liquid component is predominately an organic solvent. In certain embodiments, the alcohol is ethanol, isopropyl alcohol, or a combination thereof. As used herein, "predominant" means greater than 50 percent.

A disinfectant wipe of the present invention, comprised of a homogeneous non-woven material, has advantageous properties when wetted with a liquid component comprised predominately of an alcohol. For example, a homogeneous non-woven material of the present invention loses less strength when wet out with a liquid component comprised predominately of an alcohol according to the present invention compared to a non-woven material wet out with water.

The water soluble binder may be made from a variety of materials, including natural fibers, synthetic fibers, and any combination thereof.

The liquid component may further comprise an oil-in-water emulsion, such as one comprising cetearyl isononanoate, ceteareth-20, ceteartyl alcohol, glyceryl stearate, glycerin, cetyl palmitate, and ceteareth-12.

In another embodiment, any of the liquid components described herein further comprises a humectant (e.g., glycereth-26). In one embodiment, the liquid component comprises about 1 to about 15% w/w of a humectant (e.g., glycereth-26).

In another aspect, the present invention relates to moist wipe comprising:
a. a homogeneous fibrous material (e.g., a non-woven material) comprising one or more water soluble binders; and
b. a liquid component comprising water, an organic solvent, a multivalent (e.g., divalent) salt, a chelating agent, an emulsifier, an emollient, a humectant, a pH adjusting agent and an odor neutralizing agent.

In another aspect, the present invention relates to moist toilet tissue comprising:
a. a homogeneous fibrous material (e.g., a non-woven material) comprising one or more water soluble binders; and
b. a liquid component comprising
  i. about 65 to about 90% w/w (e.g., about 65 to about 75% w/w or about 70 to about 75% w/w) of water,
  ii. about 10 to about 35% w/w (e.g., about 10 to about 25% w/w or about 15 to about 20% w/w) of an organic solvent, and
  iii. about 1 to about 10% w/w (e.g., about 3 to about 5% w/w) of a multivalent (e.g., divalent) salt,
  iv. about 0.01 to about 1% w/w of a chelating agent,
  v. about 0.005 to about 5% w/w of an emulsifier,
  vi. about 0.005 to about 5% w/w of an emollient,
  vii. about 1 to about 15% w/w of a humectant,
  viii. about 0.01 to about 5% w/w of a pH adjusting agent, and
  ix. about 0.01 to about 5% w/w of an odor neutralizing agent.

In additional embodiments, any of the liquid components described herein further comprises one or more fragrances.

In additional embodiments, any of the liquid components described herein may further comprise magnesium aluminum silicate, xanthan gum, cornstarch, silica, and any combination thereof.

In another aspect, the present invention relates to a moist wipe comprising:
a. a homogeneous fibrous material (e.g., a non-woven material) comprising one or more water soluble binders; and
b. a liquid component comprising
  i. about 65 to about 90% w/w (e.g., about 65 to about 75% w/w or about 70 to about 75% w/w) of water,
  ii. about 10 to about 35% w/w (e.g., about 10 to about 25% w/w or about 15 to about 20% w/w) of an organic solvent, and
  iii. about 1 to about 10% w/w (e.g., about 3 to about 5% w/w) of a multivalent (e.g., divalent) salt,
  iv. about 0.1 to about 1% w/w of a first preservative;
  v. about 0.1 to about 1% w/w of a second preservative;
  vi. about 0.0001 to about 0.1% w/w of a first soothing agent;
  vii. about 0.01 to about 0.2% w/w of a pH adjusting agent;
  viii. about 0.0001 to about 0.5% w/w of a second soothing agent;
  ix. about 0.01 to about 1% w/w of a chelating agent;
  x. about 0.01 to about 5% w/w of a pH adjusting agent;
  xi. about 0.005 to about 5% w/w of an emulsifier;
  xii. about 0.01 to about 5% w/w of an odor neutralizing agent;
  xiii. about 0.01 to about 5% w/w of a fragrance;
  xiv. about 1 to about 15% w/w of a humectant; and
  xv. about 0.005 to about 5% of an emollient.

In additional embodiments, any of the moist wipes described herein exhibit one or more of the following characteristics (i)-(vi):
  (i) In additional embodiments, any of the moist wipes described herein exhibit one or more of the following characteristics (i)-(vi):
  (i) In one embodiment, any of the wipes described herein exhibit a machine direction wet tensile strength greater or equal to about 150 g/inch and a cross direction wet tensile strength of greater than about 75 g/inch. In one embodiment, the machine cross direction wet tensile strength is reduced to less than or equal to about 50 g/in and the cross direction wet tensile strength is reduced to less than or equal to about 25 g/in, after being soaked in water for any duration of time.
  (ii) In one embodiment, any of the moist toilet tissues, cleaning wipes or personal care wipes described herein exhibit a machine direction wet tensile strength greater or equal to about 150 g/inch and a cross direction wet tensile strength of greater than about 75 g/inch. In one embodiment, the machine direction wet tensile strength and the cross direction wet tensile strength is reduced such that it is no long measurable after being soaked in water for any duration of time.
  (iii) In one embodiment, any of the moist wipes described herein exhibit a machine direction wet tensile strength greater or equal to about 150 g/inch and a cross direction wet tensile strength of greater than about 75 g/inch.

In one embodiment, the moist toilet tissue, cleaning wipe or personal care wipe has a dispersion rate of greater than or equal to about 90% after a time of about 10 seconds when measured according to the FG502.R1(18) slosh box disintegration test described in the Guidelines for Assessing the Flushability of Disposable Nonwoven Products. A Process for Assessing the Compatibility of Disposable Nonwoven Products with Plumbing and Wastewater Infrastructure, 4th Edition, © INDA and EDANA, 2018, which is hereby incorporated by reference in its entirety.

In one embodiment, the moist wipe has a dispersion rate of greater than or equal to about 70% after a time of about 1 minute when measured according to the FG502.R1(18) slosh box disintegration test described in the Guidelines for Assessing the Flushability of Disposable Nonwoven Products. A Process for Assessing the Compatibility of Disposable Nonwoven Products with Plumbing and Wastewater Infrastructure, Fourth Edition, © INDA and EDANA, May 2018, which is hereby incorporated by reference in its entirety.

In one embodiment, the moist wipe has a dispersion rate of greater than or equal to about 50% after a time of about 2 minutes when measured according to the FG502.R1(18) slosh box disintegration test described in the Guidelines for Assessing the Flushability of Disposable Nonwoven Products. A Process for Assessing the Compatibility of Disposable Nonwoven Products with Plumbing and Wastewater Infrastructure, Fourth Edition, © INDA and EDANA, May 2018, which is hereby incorporated by reference in its entirety.

In one embodiment, the moist wipe has a dispersion rate of greater than or equal to about 30% after a time of about 5 minutes when measured according to the FG502.R1(18) slosh box disintegration test described in the Guidelines for Assessing the Flushability of Disposable Nonwoven Products. A Process for Assessing the Compatibility of Disposable Nonwoven Products with Plumbing and Wastewater Infrastructure, Fourth Edition, © INDA and EDANA, May 2018, which is hereby incorporated by reference in its entirety.

(iv) In one embodiment, any of the moist wipes described herein loses all tensile strength in both the machine and cross directions, when flushed in a toilet, and that falls into small pieces less than $\frac{1}{2}$ in$^2$ with the turbulence of a single flush of a standard household toilet as it goes through the toilet hole to be transferred to household pump basin, not creating any clogs in the household pump or leaving any full wipes intact remaining in the basin, when tested according to the household pump test described in INDA's Fourth Edition Flushability Guideline Document FG503.R1(18) Household Pump Test, which is hereby incorporated by reference in its entirety.

(v) In one embodiment, any of the moist wipes described herein exhibits less than about 50 g/in machine direction tensile strength and less than about 25 g/in cross direction tensile strength when soaked in water to go through a municipal pump that falls apart into pieces equal to or less than $\frac{1}{2}$ in$^2$ creating less than 2% or no power increase when tested according to the INDA's Fourth Edition Flushability Guideline Document FG507.R1(18) Municipal Sewage Pump Test, which is hereby incorporated by reference in its entirety.

(vi) In one embodiment, any of the moist wipes described herein exhibits no measurable strength when soaked in water to go through a municipal pump that falls apart into pieces equal to or less than $\frac{1}{2}$ in$^2$ creating less than 2% or no power increase when tested according to INDA's Fourth Edition Flushability Guideline Document FG507.R1(18) Municipal Sewage Pump Test, which is hereby incorporated by reference in its entirety.

In an additional embodiment, the moist wipes described herein are packaged.

The present invention provides a moist wipe comprising:
 a. a homogeneous fibrous material comprising one or more water soluble binders; and
 b. a liquid component comprising
  i. about 74% w/w of water,
  ii. about 15% w/w of dipropylene glycol,
  iii. about 5% w/w of glycereth 26, and
  iv. about 4% w/w of calcium chloride.

The liquid component may further comprise a chelating agent, an emulsifier, an emollient, a humectant, a pH adjusting agent, an odor neutralizing agent, and a fragrance.

In some aspects, the liquid component further comprises magnesium aluminum silicate, xanthan gum, cornstarch, silica, and any combination thereof.

A moist wipe of the present invention includes:
 a. a homogeneous fibrous material comprising one or more water soluble binders; and
 b. a liquid component comprising
  i. about 58 to about 79% w/w of water,
  ii. about 0 to about 10% w/w of dipropylene glycol,
  iii. about 0 to about 10% w/w of glycereth 26,
  iv. about 0 to about 4% w/w of calcium chloride, and
  vi. about 5 to about 20% w/w of ethanol.

A moist wipe of the present invention exhibits a machine direction wet tensile strength greater or equal to about 150 g/inch and a cross direction wet tensile strength of greater than about 75 g/inch. The machine direction wet tensile strength of a wipe according to the present invention is reduced to less than or equal to about 50 g/in and the cross direction wet tensile strength is reduced to less than or equal to about 25 g/in, after being soaked in water for any duration of time. In a moist wipe, cleaning wipe or personal wipe of the present invention, the machine direction wet tensile strength and the cross direction wet tensile strength are reduced such that they are no longer measurable after being soaked in water for any duration of time.

In a moist wipe, cleaning wipe or personal wipe of the present invention, the wipe has a dispersion rate of greater than or equal to about 90% after a time of about 10 seconds when measured according to INDA's Fourth Edition Flushability Guideline Document FG502.R1(18) slosh box disintegration test.

In a moist wipe, cleaning wipe or personal wipe of the present invention, the wipe has a dispersion rate of greater than or equal to about 70% after a time of about 1 minute when measured according to INDA's Fourth Edition Flushability Guideline Document FG502.R1(18) slosh box disintegration test.

In a moist wipe, cleaning wipe or personal wipe of the present invention, the wipe has a dispersion rate of greater than or equal to about 50% after a time of about 2 minutes when measured, e.g., according to INDA's Fourth Edition Flushability Guideline Document FG502.R1(18) slosh box disintegration test.

In a moist wipe, cleaning wipe or personal wipe of the present invention, the wipe has a dispersion rate of greater than or equal to about 30% after a time of about 5 minutes when measured according to INDA's Fourth Edition Flushability Guideline Document FG502.R1(18) slosh box disintegration test.

In a moist wipe, cleaning wipe or personal wipe of the present invention, the wipe loses all tensile strength in both the machine and cross directions, when flushed in a toilet, and that falls into small pieces less than $\frac{1}{2}$ in2 with the turbulence of a single flush of a standard household toilet as it goes through the toilet hole to be transferred to household pump basin, not creating any clogs in the household pump or leaving any full wipes intact remaining in the basin, when tested according to the household pump test described in INDA's Fourth Edition Flushability Guideline Document FG503.R1(18) Household Pump Test.

In a moist wipe, cleaning wipe or personal wipe of the present invention, the wipe exhibits less than about 50 g/in machine direction tensile strength and less than about 25 g/in cross direction tensile strength when soaked in water to go through a municipal pump that falls apart into pieces equal to or less than ½ in2 creating less than 2% or no power increase when tested according to the INDA's Fourth Edition Flushability Guideline Document FG507.R1(18) Municipal Sewage Pump Test.

In a moist wipe, cleaning wipe or personal wipe of the present invention, the wipe exhibits no measurable strength when soaked in water to go through a municipal pump that falls apart into pieces equal to or less than ½ in2 creating less than 2% or no power increase when tested according to INDA's Fourth Edition Flushability Guideline Document FG507.R1(18) Municipal Sewage Pump Test.

According to the present invention, the moist wipe, cleaning wipe or personal wipe of is packaged.

In an aspect, the homogeneous fibrous material is comprised of 100% plant-based materials.

In a further aspect, the liquid further comprises a quaternary ammonium compound.

A homogeneous fibrous material according to the present invention includes one or more cellulosic fibers at about 50 to about 99% w/w and one or more water soluble binders.

In aspects of the invention, the one or more cellulosic fibers comprises a pulp fiber or a regenerated cellulose fiber and the one or more water soluble binders comprises carboxymethyl cellulose.

According to aspects of the invention, the one or more cellulose fibers are present at about 75 to 99% w/w of the total weight of the wipe and the carboxymethyl cellulose is present at about 1 to about 25% w/w of the total weight of the wipe.

According to embodiments of the present invention, the regenerated cellulose fibers may be viscose, lyocell, or combinations thereof. In further aspects, the regenerated cellulose fibers are present at about 10 to about 50% w/w of the total weight of the wipe.

DETAILED DESCRIPTION OF THE INVENTION

The rate and overall dispersibility of a moist dispersible wipe may be determined by a person of ordinary skill in the art, for example, as described in Guidelines for Assessing the Flushability of Disposable Nonwoven Products. A Process for Assessing the Compatibility of Disposable Nonwoven Products with Plumbing and Wastewater Infrastructure, Fourth Edition, © INDA and EDANA, May 2018 ("the Guidelines") (see www.edana.org and www,inda,org), which is hereby incorporated by reference in its entirety.

According to the Guidelines, for a product to be deemed flushable there must be evidence indicating that it (1) clears toilets and properly maintained drainage pipe systems when the suppliers recommended usage instructions are correctly followed; (2) passes through wastewater conveyance systems and is compatible with wastewater treatment, reuse and disposal systems without causing system blockage, clogging or other operational problems; and (3) is unrecognizable in effluent leaving onsite and municipal wastewater treatment systems and in digested sludge from wastewater treatment plants that are applied to soil. When a product fulfills the requirements in this assessment, it is considered flushable and can be labeled as such in accordance with the INDA/ EDANA Code of Practice.

The Homogeneous Fibrous Component

In one embodiment, the homogeneous fibrous materials described herein comprise a nonwoven material.

As used herein the terms "nonwoven agent" or "nonwoven material" or "nonwoven substrate" of "non-woven component" refer to materials and webs of materials which are formed without the aid of a textile weaving or knitting process.

Figure 1:
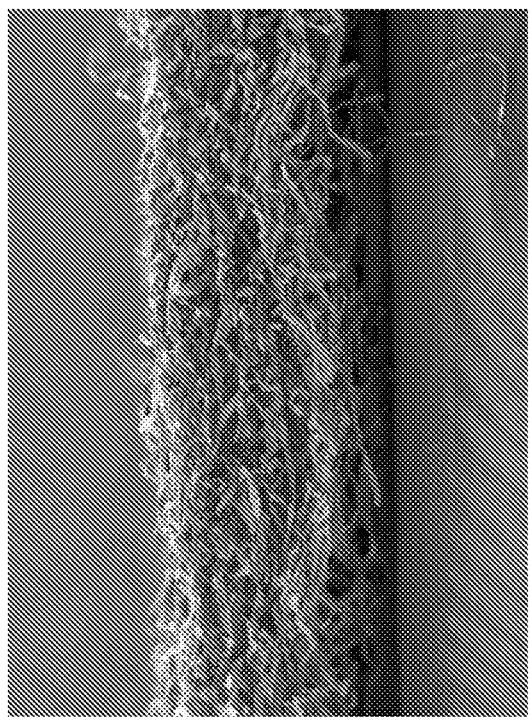
FIG. 1 is a scanning electron micrograph of a cross section of a homogeneous fibrous component.
Figure 2:
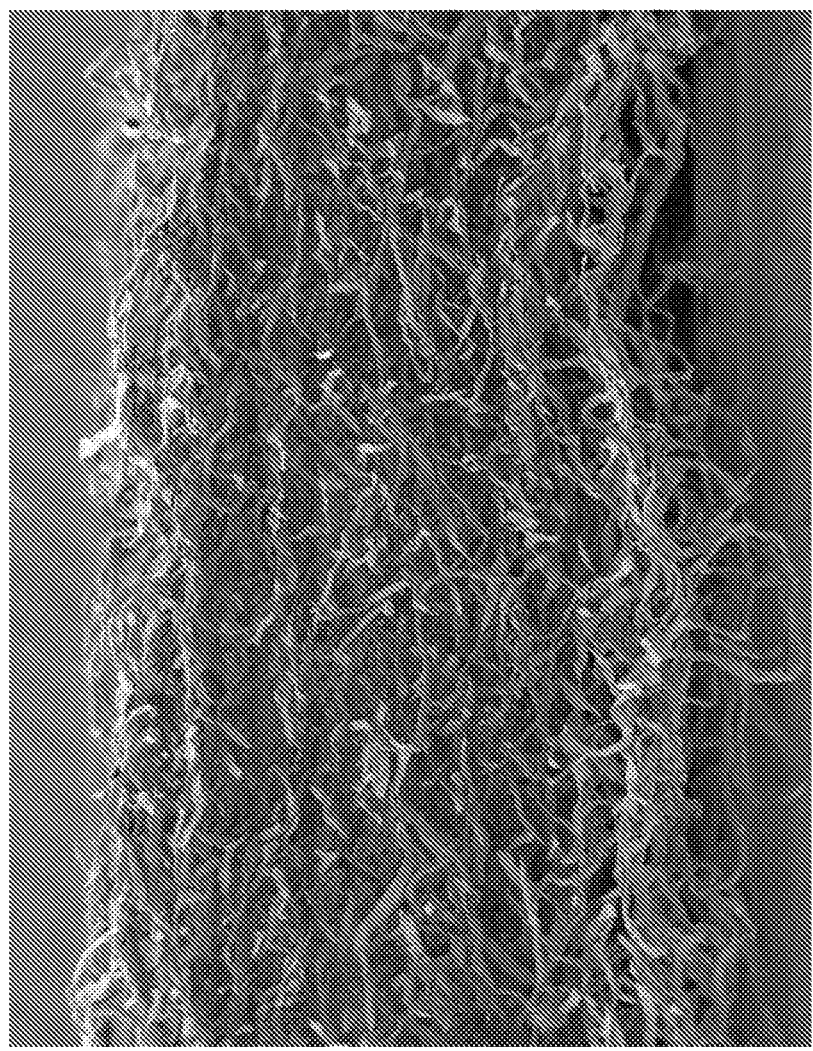
FIG. 2 is a scanning electron micrograph of a cross section of a homogeneous fibrous component.
Figure 3:
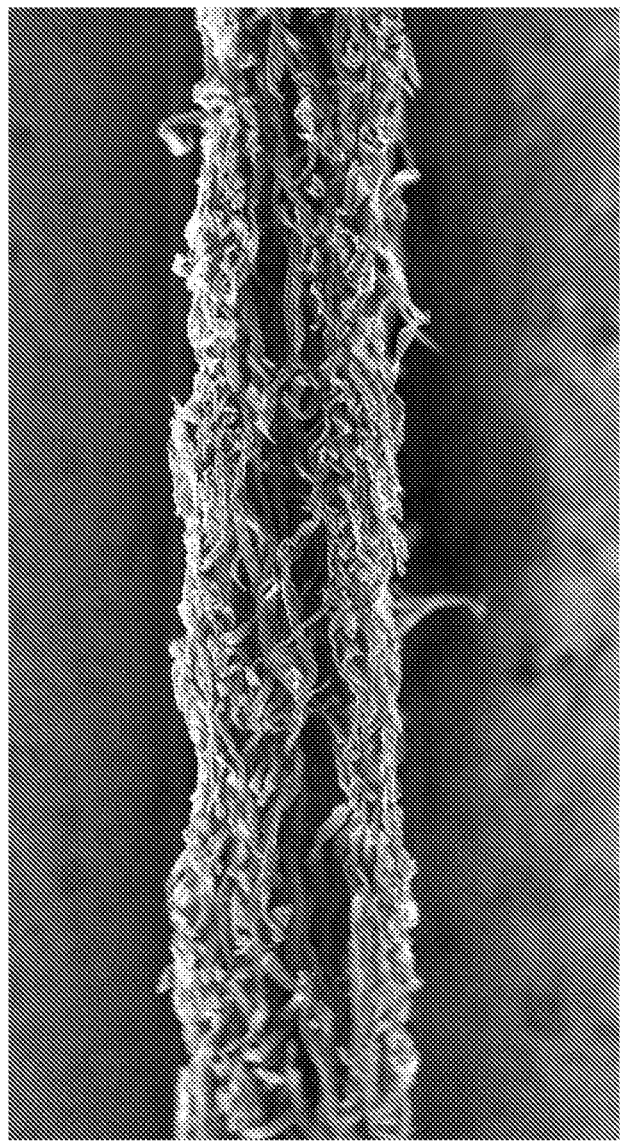
FIG. 3 is a scanning electron micrograph of a fibrous component that is not homogeneous. The non-woven moist sheet was air dried and stained with iodine vapor stain for 72 hours to highlight the binder distribution.
Figure 4:
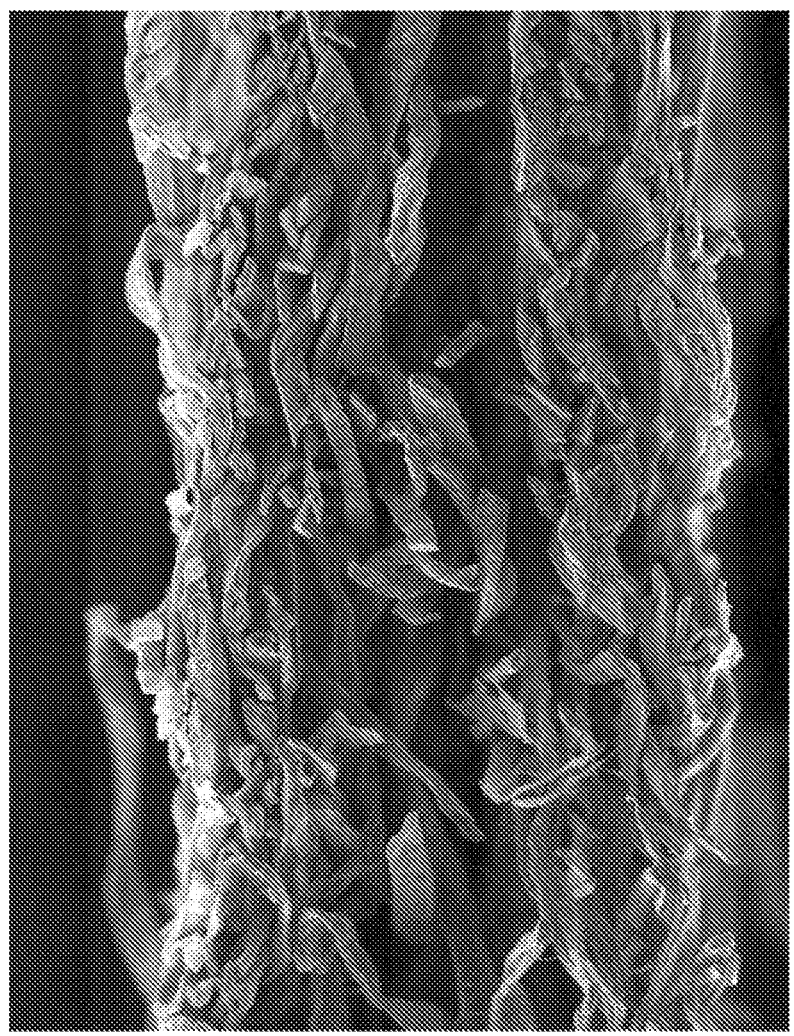
FIG. 4 is a scanning electron micrograph of a cross section of a fibrous component that is not homogeneous. The non-woven moist sheet was air dried and stained with iodine vapor stain for 72 hours to highlight the binder distribution.

As used herein, "homogeneous fibrous material," "homogeneous fibrous component," and "homogeneous nonwoven material" mean that the different constituents of the fibrous material or fibrous component are integrated and not segregated. Illustrations of "homogeneous fibrous material," "homogeneous fibrous component," and "homogeneous nonwoven material" are shown in FIGS. 1-3.

Moist toilet tissues according to the present invention may generally have a fiber density of about 0.025 g/cc to about 0.2 g/cc. Moist toilet tissues according to the present invention may generally have a basis weight of about 20 gsm to about 150 gsm, such as between about 30 to about 90 gsm or about 50 gsm to about 60 gsm.

The nonwoven materials may comprise one or more water soluble binders made from natural fibers, synthetic fibers, and any combination thereof. The choice of fibers depends upon, for example, the intended end use of the finished product and fiber cost. For instance, suitable fibrous substrates may include, but are not limited to, natural fibers such as cotton, linen, jute, hemp, wool, wood pulp, etc. Similarly, regenerated cellulosic fibers, such as viscose rayon and cuprammonium rayon, modified cellulosic fibers, such as cellulose acetate, or synthetic fibers, such as those derived from polypropylenes, polyethylenes, polyolefins, polyesters, polyamides, polyacrylics, etc., alone or in combination with one another, may likewise be used. Blends of one or more of the above fibers may also be used, if so desired. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Mercerized, chemically stiffened or crosslinked fibers may also be used.

Synthetic cellulose fiber types include rayon in all its varieties and other fibers derived from viscose or chemically modified cellulose, including regenerated cellulose and solvent-spun cellulose, such as Lyocell. Chemically treated natural cellulosic fibers can be used, such as mercerized pulps, chemically stiffened or crosslinked fibers, or sulfonated fibers. Recycled fibers, as well as virgin fibers, can be used. Cellulose produced by microbes and other cellulosic derivatives can be used. As used herein, the term "cellulosic" is meant to include any material having cellulose as a major constituent, for example, comprising at least 50 percent by weight cellulose or a cellulose derivative. Thus, the term includes, but is not limited to cotton, typical wood pulps, non-woody cellulosic fibers, carboxymethyl cellulose, cellulose acetate, cellulose triacetate, rayon, thermomechanical wood pulp, chemical wood pulp, debonded chemical wood pulp, milkweed, or bacterial cellulose. Polylactic acid (PLA), polyethylene terephthalate, polypropylene and nylon may also be used.

The nonwoven component may further comprise a surfactant. Non-limiting examples of suitable surfactants include: sodium lauryl sulfate, 1-undecanol, 1-octyl-2-pyrrolidone (SURFADONE™ LP-100), undecyl alcohol+5 EO polyethyoxylate (poly ethylene glycol (5) undecyl ether), 1-dodecyl-2-pyrrolidone (SURFADONE™ LP-300), and combinations thereof. An example of a combination of surfactants is sodium lauryl sulfate, 1-undecanol, 1-octyl-2-pyrrolidone, and undecyl alcohol+5 EO polyethyoxylate (poly ethylene glycol (5) undecyl ether). The surfactant may be added to a carboxymethyl cellulose (CMC) and water solution to be sprayed onto the fibrous material. The amount of surfactant may be from 0.001% to 2% of the CMC and water spray solution.

The Liquid Component

The liquid components described herein may be substantially free (e.g., contain less than about 0.04 wt %, less than about 0.03 wt %, less than about 0.02 wt %, less than about 0.01 wt %, or less than about 0.005 wt %) of benzalkonium chloride, or are free of benzalkonium chloride.

The liquid components described herein may be substantially free (e.g., contain less than about 0.08 wt %, less than about 0.05 wt %, less than about 0.04 wt %, less than about 0.02 wt %, less than about 0.01 wt % or less than about 0.005 wt %) of iodopropynyl butylcarbamate, or are free of iodopropynyl butylcarbamate.

Optionally, the liquid components described herein may be substantially free (e.g., contain less than about 0.03, less than about 0.02, less than about 0.01, less than about 0.005 wt % or less than about 0.001 wt %) of benzalkonium chloride, iodopropynyl butylcarbamate, laureth-9, vinyl dimethicone/methicone silsesquioxane crosspolymer, and combinations of the foregoing.

The liquid component according to the embodiments described herein may further comprise one or more additional compounds, such as, but not limited to, carrier medium(s), surfactants (e.g. cationic, anionic, nonionic, amphoteric), pH adjusting/pH control agents, fragrances, fragrance solubilizers, opacifiers, preservatives, skin soothing aids/soothing agents, skin-care additives, odor control additives/odor neutralizing agents, chelating agents, detackifying agents, wetting agents, cleaning agents, skin conditioning agents, preservatives, anti-microbial agents, emollients, humectants, sensory (surface feel) modifiers, and the like.

Non-limiting examples of chelating agents include disodium EDTA, sodium gluconate, phytic acid, sodium phytate, trisodium EDTA, tetrasodium EDTA, tetrasodium glutamate diacetate, etidronic acid, gluconic acid, pentasodium trisphosphate, sodium polyphosphate, and trisodium phosphate.

Skin-Care Additives

As used herein, the term "skin-care additives" represents additives, which provide one or more benefits to the user, such as a reduction in the probability of having diaper rash and/or other skin damage caused by fecal enzymes. Suitable skin-care additives include, but are not limited to, the enzyme inhibitors and sequestrants set forth hereafter.

A variety of skin-care additives may be added to the liquid component and the moist toilet tissues of the present invention or included therein. In one embodiment, skin-care additives in the form of particles are added to serve as fecal enzyme inhibitors, offering potential benefits in the reduction of diaper rash and skin damage caused by fecal enzymes. U.S. Pat. No. 6,051,749, discloses organophilic clays in a woven or nonwoven web, said to be useful for inhibiting fecal enzymes. Such materials may be used, including reaction products of a long chain organic quaternary ammonium compound with one or more of the following clays: montmorillonite, bentonite, beidellite, hectorite, saponite, and stevensite.

Other known enzyme inhibitors and sequestrants may be used as skin-care additives in the liquid component of the present invention, including those that inhibit trypsin and other digestive or fecal enzymes, and inhibitors for urease. For example, enzyme inhibitors and anti-microbial agents may be used to prevent the formation of odors in body fluids. For example, urease inhibitors, which are also said to play a role in odor absorption, are disclosed in International Application No. WO 98/26808. Such inhibitors may be incorporated into the liquid component and the moist toilet tissues of the present invention and include transition metal ions and their soluble salts, such as silver, copper, zinc, ferric, and aluminum salts. The anion may also provide urease inhibition, such as borate, phytate, etc. Compounds of potential value include, but are not limited to, silver chlorate, silver nitrate, mercury acetate, mercury chloride, mercury nitrate, copper metaborate, copper bromate, copper bromide, copper chloride, copper dichromate, copper nitrate, copper salicylate, copper sulfate, zinc acetate, zinc borate, zinc phytate, zinc bromate, zinc bromide, zinc chlorate, zinc chloride, zinc sulfate, cadmium acetate, cadmium borate, cadmium bromide, cadmium chlorate, cadmium chloride, cadmium formate, cadmium iodate, cadmium iodide, cadmium permanganate, cadmium nitrate, cadmium sulfate, and gold chloride.

Other salts that have urease inhibition properties include ferric and aluminum salts, especially the nitrates, and bismuth salts. Other urease inhibitors are disclosed in WO 98/26808, including hydroxamic acid and its derivatives; thiourea; hydroxylamine; salts of phytic acid; extracts of plants of various species, including various tannins, e.g. carob tannin, and their derivatives such as chlorogenic acid derivatives; naturally occurring acids such as ascorbic acid, citric acid, and their salts; phenyl phosphoro diamidate/diamino phosphoric acid phenyl ester; metal aryl phosphoramidate complexes, including substituted phosphorodiamidate compounds; phosphoramidates without substitution on the nitrogen; boric acid and/or its salts, including especially, borax, and/or organic boron acid compounds; the compounds disclosed in European Patent Application No. 0,408,199; sodium, copper, manganese, and/or zinc dithiocarbamate; quinones; phenols; thiurams; substituted rhodanine acetic acids; alkylated benzoquinones; formamidine disulphide; 1:3-diketones maleic anhydride; succinamide; phthalic anhydride; pehenic acid; /N,N-dihalo-2-imidazolidinones; N-halo2-oxazolidinones; thio- and/or acyl-phosphoryltnamide and/or substituted derivatives thereof-, thiopyridine-N-oxides, thiopyridines, and thiopyrimidines; oxidized sulfur derivatives of diarninophosphinyl compounds; cyclotriphosphazatriene derivatives; ortho-diaminophosphinyl derivatives of oximes; bromo-nitro compounds; S-aryl and/or alkyl diamidophosphorothiolates; diaminophosphinyl derivatives; mono- and/or polyphosphorodiamide; 5-substituted-benzoxathiol-2-ones; N(diaminophosphinyl)arylcarboxamides; alkoxy-1,2-benzothaizin compounds; etc.

Many other skin-care additives may be incorporated into the liquid component and moist toilet tissues of the present invention, including, but not limited to, sun blocking agents and UV absorbers, acne treatments, pharmaceuticals, baking soda (including encapsulated forms thereof), vitamins and their derivatives such as Vitamins A or E, aloe barbadenis leaf extract, tocopheryl acetate, botanicals such as witch hazel extract and aloe vera, allantoin, emollients, disinfectants, hydroxy acids for wrinkle control or anti-aging effects, sunscreens, tanning promoters, skin lighteners, deodorants and anti-perspirants, ceramides for skin benefits and other uses, astringents, moisturizers, nail polish removers, insect repellants, antioxidants, antiseptics, anti-inflammatory agents and the like, provided that the additives are compatible with an ion-sensitive binder composition associated therewith, and especially the ion-sensitive binder compositions of the present invention (i.e., they do not cause a substantial loss of strength in the wet state of the moist toilet tissues, prior to dilution in water, while permitting dispersibility in water).

Useful materials for skin care and other benefits are listed in McCutcheon's 1999, Vol. 2: Functional Materials, MC Publishing Company, Glen Rock, N.J. Many useful botanicals for skin care are provided by Active Organics, Lewisville, Tex.

Odor Control Additives

Suitable odor control additives for use in the liquid component and moist toilet tissues of the present invention include, but are not limited to, zinc salts; talc powder; sodium bicarbonate, encapsulated perfumes (including microcapsules, macrocapsules, and perfume encapsulated in liposomes, vessicles, or microemulsions); chelants, such as ethylenediamine tetra-acetic acid; zeolites; activated silica, activated carbon granules or fibers; activated silica particulates; polycarboxylic acids, such as citric acid; cyclodextrins and cyclodextrin derivatives; chitosan or chitin and derivatives thereof; oxidizing agents; antimicrobial agents, including silver-loaded zeolites (e.g., those of BF Technologies, Beverly, Massachusetts, sold under the trademark HEALTHSHIELD™); triclosan; kieselguhr; and mixtures thereof. In addition to controlling odor from the body or body wastes, odor control strategies can also be employed to mask or control any odor of the treated substrate.

In one embodiment of, the liquid component and/or moist wipes comprise derivatized cyclodextrins, such as hydroxypropyl beta-cyclodextrin in solution, which remain on the skin after wiping and provide an odor-absorbing layer. In other embodiments, the odor source is removed or neutralized by application of an odor-control additive, exemplified by the action of a chelant that binds metal groups necessary for the function of many proteases and other enzymes that commonly produce an odor. Chelating the metal group interferes with the enzyme's action and decreases the risk of malodor in the product.

Principles for the application of chitosan or chitin derivatives to nonwoven webs and cellulosic fibers are described in S. Lee et al., *Textile Research Journal*, 69(2); 104-112, 1999.

Detackifying Agents

Detackifying agents may be used in the liquid component to reduce the tackiness, if required. Suitable detackifiers include, but are not limited to, powders, such as talc powder, calcium carbonate, mica; starches, such as corn starch; lycopodium powder; mineral fillers, such as titanium dioxide; silica powder; alumina; metal oxides in general; baking powder; kieselguhr; and the like. Polymers and other additives having low surface energy may also be used, including a wide variety of fluorinated polymers, silicone additives, polyolefins (e.g., polytetrafluoroethylene (PTFE)) and thermoplastics, waxes, debonding agents known in the paper industry including compounds having alkyl side chains such as those having 16 or more carbons, and the like. Compounds used as release agents for molds and candle making may also be considered, as well as, dry lubricants and fluorinated release agents.

Preservatives and Anti-Microbial Agents

The liquid component may also contain preservatives and/or anti-microbial agents. Several preservatives and/or anti-microbial agents, such as Mackstat H 66 (available from McIntyre Group, Chicago, Ill.), have been found to give excellent results in preventing bacteria and mold growth. Other suitable preservatives and anti-microbial agents include, but are not limited to DMDM hydantoin (e.g., Glydant Plus™, Lonza, Inc., Fair Lawn, N.J.), iodopropynyl butylcarbamate, Kathon (Rohm and Hass, Philadelphia, Pa.), methylparaben, phenoxyethanol, sodium benzoate, propylparaben, 2-bromo-2-nitropropane-1,3-diol, benzoic acid, and the like.

Chelating Agents

One chelating agent useful in the liquid components described herein is tetrasodium glutamate diacetate (DISSOLVINE® GL 47S).

Emulsifiers

One emulsifier and surfactant blend useful in the liquid component described herein is cocoglucoside/glycerol oleate (LAMESOFT® P065).

Wetting Agents and Cleaning Agents

A variety of wetting agents and/or cleaning agents may be used in the liquid component. Suitable wetting agents and/or cleaning agents include, but are not limited to, detergents and nonionic, amphoteric, and anionic surfactants, especially amino acid-based surfactants. Amino acid-based surfactant systems, such as those derived from amino acids L-glutamic acid and other natural fatty acids, offer pH compatibility to human skin and good cleansing power, while being relatively safe and providing improved tactile and moisturization properties compared to other anionic surfactants.

One commercial example of an amino-acid based surfactant is acylglutamate, marketed under the Amisoft name by Ajinomoto Corp., Tokyo, Japan. Although amino-acid based surfactant may be useful in the liquid components, a wide variety of surfactants may be used in the present invention. Suitable non-ionic surfactants include, but are not limited to, the condensation products of ethylene oxide with a hydrophobic (oleophilic) polyoxyalkylene base formed by the condensation of propylene oxide with propylene glycol. The hydrophobic portion of these compounds desirably has a molecular weight sufficiently high so as to render it water-insoluble. The addition of polyoxyethylene moieties to this hydrophobic portion increases the water-solubility of the molecule as a whole, and the liquid character of the product is retained up to the point where the polyoxyethylene content is about 50% of the total weight of the condensation product. Examples of compounds of this type include commercially-available Pluronic surfactants (BASF Wyandotte Corp.), such as those in which the polyoxypropylene ether has a molecular weight of about 1500-3000 and the polyoxyethylene content is about 35-55% of the molecule by weight, i.e. Pluronic L-62.

Other useful nonionic surfactants include, but are not limited to, the condensation products of $C_8$-$C_{22}$ alkyl alcohols with 2-50 moles of ethylene oxide per mole of alcohol. Examples of compounds of this type include the condensation products of $C_{11}$-$C_{15}$ secondary alkyl alcohols with 3-50 moles of ethylene oxide per mole of alcohol, which are commercially-available as the Poly-Tergent SLF series from Olin Chemicals or the TERGITOL™ series from Union Carbide, i.e. TERGITOL™ 25-L-7, which is formed by condensing about 7 moles of ethylene oxide with a $C_{12}$-$C_{15}$ alkanol.

Other nonionic surfactants, which may be employed in the liquid component of the present invention, include the ethylene oxide esters of $C_6$-$C_{12}$ alkyl phenols such as (nonylphenoxy)polyoxyethylene ether. Particularly useful are the esters prepared by condensing about 8-12 moles of ethylene oxide with nonylphenol, i.e. the IGEPAL™ CO series (GAF Corp.).

Further non-ionic surface active agents include, but are not limited to, alkyl polyglycosides (APG), derived as a condensation product of dextrose (D-glucose) and a straight or branched chain alcohol. The glycoside portion of the surfactant provides a hydrophile having high hydroxyl density, which enhances water solubility. Additionally, the inherent stability of the acetal linkage of the glycoside provides chemical stability in alkaline systems. Furthermore, unlike some non-ionic surface active agents, alkyl polyglycosides have no cloud point, allowing one to formulate without a hydrotrope, and these are very mild, as well as readily biodegradable non-ionic surfactants. This class of surfactants is available from Horizon Chemical under the trade names of APG-300, APG-350, APG-500, and APG-500.

Silicones are another class of wetting agents available in pure form, or as microemulsions, macroemulsions, and the like. One exemplary non-ionic surfactant group is the silicone-glycol copolymers. These surfactants are prepared by adding poly(lower)alkylenoxy chains to the free hydroxyl groups of dimethylpolysiloxanols and are available from the Dow Corning Corp as DOW CORNING® 190 and 193 surfactants (CTFA name: dimethicone copolyol).

Anionic surfactants may also be used in the liquid components described herein. Anionic surfactants are useful due to their high detergency include anionic detergent salts having alkyl substituents of 8 to 22 carbon atoms such as the water-soluble higher fatty acid alkali metal soaps, e.g., sodium myristate and sodium palmitate. One class of anionic surfactants encompasses the water-soluble sulfated and sulfonated anionic alkali metal and alkaline earth metal detergent salts containing a hydrophobic higher alkyl moiety (typically containing from about 8 to 22 carbon atoms) such as salts of higher alkyl mono or polynuclear aryl sulfonates having from about 1 to 16 carbon atoms in the alkyl group, with examples available as the BIO-SOFT® series, i.e. BIO-SOFT® D-40 (Stepan Chemical Co.) (sodium salt of linear alkylbenzene sulfonic acid).

Other useful classes of anionic surfactants include, but are not limited to, the alkali metal salts of alkyl naphthalene sulfonic acids (methyl naphthalene sodium sulfonate, Petro AA, Petrochemical Corporation); sulfated higher fatty acid monoglycerides such as the sodium salt of the sulfated monoglyceride of cocoa oil fatty acids and the potassium salt of the sulfated monoglyceride of tallow fatty acids; alkali metal salts of sulfated fatty alcohols containing from about 10 to 18 carbon atoms (e.g., sodium lauryl sulfate and sodium stearyl sulfate); sodium $C_{14}$-$C_{16}$-alphaolefin sulfonates such as the BIO-TERGE® series (Stepan Chemical Co.); alkali metal salts of sulfated ethyleneoxy fatty alcohols (the sodium or ammonium sulfates of the condensation products of about 3 moles of ethylene oxide with a $C_{12}$-$C_{15}$ n-alkanol, i.e., the Neodol ethoxysulfates, Shell Chemical Co.); alkali metal salts of higher fatty esters of low molecular weight alkylol sulfonic acids, e.g. fatty acid esters of the sodium salt of isothionic acid, the fatty ethanolamide sulfates; the fatty acid amides of amino alkyl sulfonic acids, e.g. lauric acid amide of taurine; as well as numerous other anionic organic surface active agents such as sodium xylene sulfonate, sodium naphthalene sulfonate, sodium toulene sulfonate and mixtures thereof.

A further class of anionic surfactants includes the 8-(4-n-alkyl-2-cyclohexenyl)-octanoic acids, wherein the cyclohexenyl ring is substituted with an additional carboxylic acid group. These compounds or their potassium salts, are commercially-available from Westvaco Corporation as Diacid 1550 or H-240. In general, these anionic surface active agents can be employed in the form of their alkali metal salts, ammonium or alkaline earth metal salts.

Emollients

The liquid component may also contain one or more emollients. Suitable emollients include, but are not limited to, PEG 75 lanolin, caprylic/capric triglyceride, methyl gluceth 20 benzoate, $C_{12}$-$C_{15}$ alkyl benzoate, ethoxylated cetyl stearyl alcohol, products marketed as LAMBENT WAX® WS-L (nonionic, water-soluble, silicone copolyol wax), LAMBENT® WD-F, CETIOL® HE (Henkel Corp.) (PEG-7 Glyceryl Cocoate), GLUCAM™ P20 (PPG-20 Methyl Glucose Ether, POLYOX™ WSR N-10 (PEG-2M), POLYOX™ WSR N-3000 (PEG-14M), LUVIQUAT® (BASF) (Polyquaternium-16), FINSOLV® SLB 101 (Dimethicone PEG/PPG-20/23 Benzoate), mink oil, allantoin, stearyl alcohol, Estol 1517 (isopropyl palmitate) (UNICHEMA®), and FINSOLV® SLB 201 (Dimethicone PEG-8 Benzoate), glyceryl oleate (MONOMULS® 90-O 18, BASF), and combinations thereof.

The emollient may be in the form of an emollient blend. For example, the emollient blend comprises a combination of one or more liquid hydrocarbons (e.g., petrolatum), mineral oil and the like, vegetable and animal fats (e.g., lanolin, phospholipids and their derivatives), with a silicone material such as one or more alkyl substituted polysiloxane polymers. The emollient blend may comprise a combination of liquid hydrocarbons (e.g., petrolatum) with dimethicone or with dimethicone and other alkyl substituted polysiloxane polymers. In some embodiments, blends of liquid hydrocarbon emollients and/or alkyl substituted polysiloxane polymers may be blended with one or more fatty acid ester emollients derived from fatty acids or fatty alcohols. PEG-7 glyceryl cocoate.

Water-soluble, self-emulsifying emollient oils which may be used in the liquid component include the polyoxyalkoxylated lanolins and the polyoxyalkoxylated fatty alcohols, as disclosed in U.S. Pat. No. 4,690,821. The polyoxyalkoxy chains may comprise mixed propylenoxy and ethyleneoxy units. The lanolin derivatives may comprise about 20-70 such lower-alkoxy units while the $C_{12}$-$C_{20}$-fatty alcohols will be derivatized with about 8-15 lower-alkyl units. One such lanolin derivative is LANEXOL™ AWS (PPG-12-PEG-50, Croda, Inc., New York, N.Y.). A useful poly(15-20)$C_2$-$C_3$-alkoxylate is PPG-5-Ceteth-20, known as PROCETYL™ AWS (Croda, Inc.).

Surface Feel Modifiers

Surface feel modifiers may be used to improve the tactile sensation (e.g., lubricity) of the skin during use of the product. Suitable surface feel modifiers include, but are not limited to, commercial debonders; and softeners, including quaternary ammonium compounds with fatty acid side groups, silicones, waxes, and the like. Exemplary quaternary ammonium compounds with utility as softeners are disclosed in U.S. Pat. Nos. 3,554,862, 4,144,122, 5,573,637, and 4,476,323.

Fragrances and Fragrance Solubilizers

A variety of fragrances and fragrance solubilizers may be used in the liquid component. Suitable fragrance solubilizers include, but are not limited to, polysorbate 20, propylene glycol, ethanol, isopropanol, diethylene glycol monoethyl ether, dipropylene glycol, diethyl phthalate, triethyl citrate, Ameroxol OE-2 (Amerchol Corp.), BRIJ™ 78 and BRIJ™ 98 (ICI Surfactants), ARLASOLVE® 200 (ICI Surfactants), CALFAX® 16L-35 (Sodium Hexadecyl Diphenyl Oxide Disulfonate) (Pilot Chemical Co.), CAPMUL® POE-S (Abitec Corp.), FINSOLV® SUBSTANTIAL (Finetex), and the like.

Opacifiers

Suitable opacifiers include, but are not limited to, titanium dioxide or other minerals or pigments, and synthetic opacifiers such as REACTOPAQUE™ particles (available from Sequa Chemicals, Inc., Chester, S.C.).

pH Control Agents

Suitable pH control agents for use in the liquid component include, but are not limited to, malic acid, citric acid, hydrochloric acid, acetic acid, sodium hydroxide, sodium citrate, potassium hydroxide, and the like. An appropriate pH range minimizes the amount of skin irritation resulting from the liquid component on the skin.

In one embodiment, the pH of the liquid component is between about 1 and about 14, such as between about 2 and about 10, between about 4.5 and about 6.5, between about 4.7 and about 6.3 or between about 4.7 and about 5.2. In one embodiment, the pH is about 4.7. In another embodiment, the pH is about 6.3.

Suitable examples of liquid component formulations according to the present invention are shown in Table 1 below. Without limitation, any disclosure described for any one of Ranges 1-3, and any combination thereof, may be combined into a single exemplary formulation. For example, a liquid formulation may contain, in part, 68-75 w/w % water and 10-25 w/w % organic solvent.

TABLE 1

| Component | Range 1 (w/w %) | Range 2 (w/w %) | Range 3 (w/w %) |
| --- | --- | --- | --- |
| Water | 65-95 | 65-75 | 70-75 |
| Organic Solvent | 10-35 | 12-25 | 10-20 |
| Multivalent salt | 1-10 | 3-5 | 3.8-4.2 |
| First Preservative | 0.1-1.0 | 0.4-1.0 | 0.65-0.75 |
| Second Preservative | 0.1-1.0 | 0.4-0.8 | 0.4-0.6 |
| First Soothing Agent | 0.0001-0.1 | 0.0005-0.02 | 0.0005-0.01 |
| First pH Adjusting Agent | 0.01-0.2 | 0.015-0.1 | 0.02-0.05 |
| Second Soothing Agent | 0.0001-0.5 | 0.0005-0.1 | 0.0005-0.0015 |
| Chelating Agent | 0.01-1.0 | 0.05-0.5 | 0.05-0.15 |
| Second pH Adjusting Agent | 0.01-5.00 | 0.05-0.50 | 0.05-0.20 |
| Emulsifier | 0.005-5.00 | 0.005-0.50 | 0.005-0.015 |
| Odor Neutralizing Agent | 0.01-5.00 | 0.05-0.50 | 0.05-0.20 |
| Fragrance | 0.01-5.00 | 0.05-0.50 | 0.05-0.15 |
| Humectant | 1-15 | 1-10 | 4-6 |
| Emollient | 0.005-5.00 | 0.005-0.50 | 0.005-0.015 |
| Magnesium Aluminum Silicate | 0.0-2.0 | 0.0-1.0 | 0.0-0.05 |
| Xanthan Gum | 0.0-1.0 | 0.0-0.5 | 0.0-0.3 |
| Cornstarch | 0.0-5.0 | 0.0-3.5 | 0.0-3.0 |
| Silica | 0.0-1.0 | 0.0-0.5 | 0.0-0.4 |

Method of Making Moist Wipes

The liquid component may be applied to the homogeneous nonwoven material by means known in the art. Suitable means for applying the liquid component include, but are not limited to, perforated tubes, printing, spraying, electrostatic spraying, metered press rolls and impregnation. The amount of liquid component may be metered and distributed uniformly onto the homogeneous fibrous material or may be non-uniformly distributed onto the homogeneous fibrous material.

The liquid component to nonwoven fiber ratio may be between about 1.5 and about 7.5, such as between about 2.0 and about 3.5 or between about 2.0 and about 3.0.

A number of techniques readily known to a person of ordinary skill may be employed to manufacture the moist wipes. In one embodiment, these techniques may include the following steps:

1. Providing the homogeneous nonwoven material;
2. Applying a liquid component as described in any embodiment herein to the homogeneous nonwoven material to generate the moist toilet tissue (which may be performed by wetting the sheets one by one or by spraying/showering the dry stack or roll with the liquid component); and
3. Placing the moist toilet tissue in roll form or in a stack and packaging the product.

The description of the present embodiments of the invention has been presented for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention. Patents and publications cited herein are incorporated by reference in their entirety.

EXAMPLES

DISSOLVINE® GL 47S (tetrasodium glutamate diacetate) is a biodegradable chelate and is available from, e.g., Akzo Nobel Personal Care.

LAMESOFT® PO65 is a composite of coco-glucoside and glycerol oleate and is available from, e.g., Care Chemicals, Germany.

Glycereth-26 is a 26 mole ethoxylate of glycerin, and is available from, e.g., Lipo Chemicals, Inc., Paterson, NJ.

Exemplary Slosh Tube Method

Samples are aged for at least 1 week in the developmental liquid and then sloshed for 15 minutes at room temperature at 26 rpm in 2 L of tap water.

Each 4 inch tube (approximately 20 inch long) is filled with 1 L of tap water, a single wipe, and then capped at both ends. The test is performed by placing 9 tubes at once on the slosh box equipment. The slosh box was run for a determined time period (e.g., 15, 30, 45 or 60 minutes). Once the box had run for the designated amount of time, the tubes are uncapped. To collect the remains of each tube, the tube are emptied over the same sieve used during normal slosh box testing. The samples are not rinsed. All remains that did not pass through the sieve are carefully removed from the face of the sieve and collected in a weigh boat. All tubes are emptied in the same manner and the remains were weighed. The post slosh dry weight of the material is compared to the pre slosh dry weight of a wipe to determine dispersion percentage.

Example 1—Exemplary Liquid Component Formulation

TABLE 2

| Water |
| --- |
| Organic Solvent |
| Multivalent salt |
| First Preservative |
| Second Preservative |
| First Soothing Agent |
| First pH Adjusting Agent |
| Second Soothing Agent |
| Chelating Agent |
| Second pH Adjusting Agent |
| Emulsifier |
| Odor Neutralizing Agent |
| Fragrance |
| Humectant |
| Emollient |

Example 2—Products with Ethanol or Isopropyl Alcohol as the Predominant Liquid

TABLE 3

|   | Weight % Water | Weight % Isopropyl Alcohol | Weight % Ethanol | Add on level of the liquid by weight to the nonwoven | Wet Tensile Strength (grams per inch) |
| --- | --- | --- | --- | --- | --- |
| 1 | 30 | 70 | 0 | 300% | 138 |
| 2 | 30 | 70 | 0 | 300% | 172 |
| 3 | 30 | 70 | 0 | 300% | 159 |
| 4 | 30 | 70 | 0 | 300% | 175 |
| 5 | 30 | 0 | 70 | 300% | 655 |
| 6 | 30 | 0 | 70 | 300% | 636 |
| 7 | 30 | 0 | 70 | 300% | 808 |
| 8 | 30 | 0 | 70 | 300% | 665 |
| 9 | 30 | 0 | 70 | 500% | 940 |
| 10 | 30 | 0 | 70 | 500% | 1054 |
| 11 | 30 | 0 | 70 | 500% | 994 |

Example 3—Tensile Strength

As summarized in Table 3 below, tensile strength was assessed for a moist wipe including a liquid component of the invention (1) and a typical moist toilet tissue (MTT) (last column). Formulation (1) of the present invention, when used with a nonwoven component, provides the required functional tensile strength. The typical MTT formula and nonwoven component failed as it is too weak to be functional. The remaining test formulations each have at least one key ingredient removed. These key ingredients are calcium chloride, dipropylene glycol, and glycereth-26 (polyethylene glycol ether of glycerin with an average ethoxylation value of 26). As one or more of the ingredients was removed, the strength of the nonwoven decreased and rendering the product unacceptable.

The homogeneous fibrous material used in wipes 1 and A-E contains cellulosic fibers and a carboxymethyl cellulose binder. The homogeneous fibrous material used in the Typical Formulation is entirely cellulosic fibers.

TABLE 4

| INCI Name | 1 % W/W | A % W/W | B % W/W | C % W/W | D % W/W | E % W/W | Typical Formulation % W/W |
| --- | --- | --- | --- | --- | --- | --- | --- |
| Water | 73.8739 | 77.8739 | 88.8739 | 78.8739 | 93.8739 | 97.8739 | 97.8450 |
| Dipropylene Glycol | 15.0000 | 15.0000 | 0.0000 | 15.0000 | 0.0000 | 0.0000 |  |
| Glycerth-26 | 5.0000 | 5.0000 | 5.0000 | 0.0000 | 0.0000 | 0.0000 |  |
| Calcium Chloride | 4.0000 | 0.0000 | 4.0000 | 4.0000 | 4.0000 | 0.0000 |  |
| Tetrasodium Glutamate Diacetate | 0.1000 | 0.1000 | 0.1000 | 0.1000 | 0.1000 | 0.1000 | 0.2000 |
| Sodium Benzoate | 0.5000 | 0.5000 | 0.5000 | 0.5000 | 0.5000 | 0.5000 | 0.4000 |
| Lactic Acid | 0.0881 | 0.0881 | 0.0881 | 0.0881 | 0.0881 | 0.0881 |  |
| Sodium Lactate | 0.0150 | 0.0150 | 0.0150 | 0.0150 | 0.0150 | 0.0150 |  |
| Sodium Bicarbonate | 0.0010 | 0.0010 | 0.0010 | 0.0010 | 0.0010 | 0.0010 | 0.0010 |
| Polysorbate 20 | 0.5000 | 0.5000 | 0.5000 | 0.5000 | 0.5000 | 0.5000 |  |
| Phenoxyethanol | 0.7000 | 0.7000 | 0.7000 | 0.7000 | 0.7000 | 0.7000 |  |
| Coco Glucoside, GlyerylOleate (Lamesoft PO65) | 0.0100 | 0.0100 | 0.0100 | 0.0100 | 0.0100 | 0.0100 |  |
| Fragrance | 0.2000 | 0.2000 | 0.2000 | 0.2000 | 0.2000 | 0.2000 | 0.2000 |
| Caprylic/Capric Triglyceride | 0.0100 | 0.0100 | 0.0100 | 0.0100 | 0.0100 | 0.0100 |  |
| Aloe Barbadensis Leaf Extract | 0.0010 | 0.0010 | 0.0010 | 0.0010 | 0.0010 | 0.0010 |  |
| Tocopheryl Acetate | 0.0010 | 0.0010 | 0.0010 | 0.0010 | 0.0010 | 0.0010 | 0.0005 |
| Decyl Glucoside |  |  |  |  |  |  | 0.0010 |
| Sodium Citrate |  |  |  |  |  |  | 0.1200 |
| Citric Acid |  |  |  |  |  |  | 0.2300 |
| Gluconic Acid, 50% |  |  |  |  |  |  | 1.0000 |

TABLE 4-continued

| INCI Name | 1 % W/W | A % W/W | B % W/W | C % W/W | D % W/W | E % W/W | Typical Formulation % W/W |
|---|---|---|---|---|---|---|---|
| Cucumber Extract | | | | | | | 0.0010 |
| Aloe, Calendula, Chamomile, Licorice Extract Blend | | | | | | | 0.0010 |
| Total | 100.0000 | 100.000 | 100.0000 | 100.0000 | 100.0000 | 100.0000 | 100.0000 |
| Tensile strength* | Pass | Fail | Fail | Fail | Fail | Fail | Fail |
| Machine Direction average | 522 | 51 | 82 | 304 | 32 | 32 | 34 |
| Cross Direction average | 457 | 60 | 80 | 358 | 26 | 27 | 32 |

*based on 24 hour data on trial nonwoven

Table 5 below shows that adding ethanol to replace some of the water maintains or increases tensile strength. Ethanol further allows for a reduction in dipropylene glycol, which enhances the aesthetics of the wipe.

TABLE 5

| INCI Name | 1 % W/W | A % W/W | B % W/W | C % W/W | D % W/W | E % W/W | F % W/W |
|---|---|---|---|---|---|---|---|
| Water | 73.8739 | 73.8739 | 68.8739 | 63.8739 | 62.8739 | 82.8739 | 62.8739 |
| Dipropylene Glycol | 15.0000 | 0.0000 | 10.0000 | 15.0000 | 15.0000 | 0.0000 | 15.0000 |
| Glycerth-26 | 5.0000 | 5.0000 | 0.0000 | 0.0000 | 5.0000 | 0.0000 | 5.0000 |
| Calcium Chloride | 4.0000 | 4.0000 | 4.0000 | 4.0000 | 0.0000 | 0.0000 | 0.0000 |
| Ethanol | 0.0000 | 15.0000 | 15.0000 | 15.0000 | 15.0000 | 15.0000 | 15.0000 |
| Tetrasodium Glutamate Diacetate | 0.1000 | 0.1000 | 0.1000 | 0.1000 | 0.1000 | 0.1000 | 0.1000 |
| Sodium Benzoate | 0.5000 | 0.5000 | 0.5000 | 0.5000 | 0.5000 | 0.5000 | 0.5000 |
| Lactic Acid | 0.0881 | 0.0881 | 0.0881 | 0.0881 | 0.0881 | 0.0881 | 0.0881 |
| Sodium Lactate | 0.0150 | 0.0150 | 0.0150 | 0.0150 | 0.0150 | 0.0150 | 0.0150 |
| Sodium Bicarbonate | 0.0010 | 0.0010 | 0.0010 | 0.0010 | 0.0010 | 0.0010 | 0.0010 |
| Polysorbate 20 | 0.5000 | 0.5000 | 0.5000 | 0.5000 | 0.5000 | 0.5000 | 0.5000 |
| Phenoxyethanol | 0.7000 | 0.7000 | 0.7000 | 0.7000 | 0.7000 | 0.7000 | 0.7000 |
| Coco Glucoside, GlyerylOleate (Lamesoft PO65) | 0.0100 | 0.0100 | 0.0100 | 0.0100 | 0.0100 | 0.0100 | 0.0100 |
| Fragrance | 0.2000 | 0.2000 | 0.2000 | 0.2000 | 0.2000 | 0.2000 | 0.2000 |
| Caprylic/Capric Triglyceride | 0.0100 | 0.0100 | 0.0100 | 0.0100 | 0.0100 | 0.0100 | 0.0100 |
| Aloe Barbadensis Leaf Extract | 0.0010 | 0.0010 | 0.0010 | 0.0010 | 0.0010 | 0.0010 | 0.0010 |
| Tocopheryl Acetate | 0.0010 | 0.0010 | 0.0010 | 0.0010 | 0.0010 | 0.0010 | 0.0010 |
| Decyl Glucoside | | | | | | | |
| Sodium Citrate | | | | | | | |
| Citric Acid | | | | | | | |
| Gluconic Acid, 50% | | | | | | | |
| Cucumber Extract | | | | | | | |
| Aloe, Calendula, Chamomile, Licorice Extract Blend | | | | | | | |
| Total | 100.0000 | 100.000 | 100.0000 | 100.0000 | 100.0000 | 100.0000 | 100.0000 |
| Tensile strength* | Pass | Pass | Pass | Pass | Fail | Fail | Pass |
| Machine Direction average | 522 | 51 | 82 | 304 | 32 | 32 | |
| Cross Direction average | 457 | 60 | 80 | 358 | 26 | 27 | |

| INCI Name | G % W/W | H % W/W | I % W/W | J % W/W | K % W/W | L % W/W |
|---|---|---|---|---|---|---|
| Water | 58.8739 | 63.8739 | 68.8739 | 73.8739 | 63.8739 | 78.8739 |
| Dipropylene Glycol | 10.0000 | 5.0000 | 0.0000 | 5.0000 | 5.0000 | 0.0000 |
| Glycerth-26 | 10.0000 | 10.0000 | 10.0000 | 5.0000 | 5.0000 | 5.0000 |
| Calcium Chloride | 4.0000 | 4.0000 | 4.0000 | 4.0000 | 4.0000 | 4.0000 |
| Ethanol | 15.0000 | 15.0000 | 15.0000 | 10.0000 | 10.0000 | 10.0000 |
| Tetrasodium Glutamate Diacetate | 0.1000 | 0.1000 | 0.1000 | 0.1000 | 0.1000 | 0.1000 |

TABLE 5-continued

| | | | | | | |
|---|---|---|---|---|---|---|
| Sodium Benzoate | 0.5000 | 0.5000 | 0.5000 | 0.5000 | 0.5000 | 0.5000 |
| Lactic Acid | 0.0881 | 0.0881 | 0.0881 | 0.0881 | 0.0881 | 0.0881 |
| Sodium Lactate | 0.0150 | 0.0150 | 0.0150 | 0.0150 | 0.0150 | 0.0150 |
| Sodium Bicarbonate | 0.0010 | 0.0010 | 0.0010 | 0.0010 | 0.0010 | 0.0010 |
| Polysorbate 20 | 0.5000 | 0.5000 | 0.5000 | 0.5000 | 0.5000 | 0.5000 |
| Phenoxyethanol | 0.7000 | 0.7000 | 0.7000 | 0.7000 | 0.7000 | 0.7000 |
| Coco Glucoside, GlyerylOleate (Lamesoft PO65) | 0.0100 | 0.0100 | 0.0100 | 0.0100 | 0.0100 | 0.0100 |
| Fragrance | 0.2000 | 0.2000 | 0.2000 | 0.2000 | 0.2000 | 0.2000 |
| Caprylic/Capric Triglyceride | 0.0100 | 0.0100 | 0.0100 | 0.0100 | 0.0100 | 0.0100 |
| Aloe Barbadensis Leaf Extract | 0.0010 | 0.0010 | 0.0010 | 0.0010 | 0.0010 | 0.0010 |
| Tocopheryl Acetate | 0.0010 | 0.0010 | 0.0010 | 0.0010 | 0.0010 | 0.0010 |
| Decyl Glucoside | | | | | | |
| Sodium Citrate | | | | | | |
| Citric Acid | | | | | | |
| Gluconic Acid, 50% | | | | | | |
| Cucumber Extract | | | | | | |
| Aloe, Calendula, Chamomile, Licorice Extract Blend | | | | | | |
| Total | 100.0000 | 100.000 | 100.0000 | 100.0000 | 100.0000 | 100.0000 |
| Tensile strength* | Pass | Pass | Pass | Pass | Pass | Fail |
| Machine Direction average | 863 | 771 | 700 | 523 | 805 | 350 |
| Cross Direction average | 794 | 717 | 655 | 481 | 674 | 312 |

| INCI Name | M % W/W | N % W/W | O % W/W | P % W/W | Typical Formulation % W/W |
|---|---|---|---|---|---|
| Water | 68.8739 | 73.8739 | 68.8739 | 63.8739 | 97.8450 |
| Dipropylene Glycol | 0.0000 | 10.0000 | 10.0000 | 10.0000 | |
| Glycerth-26 | 5.0000 | 5.0000 | 5.0000 | 5.0000 | |
| Calcium Chloride | 4.0000 | 4.0000 | 4.0000 | 4.0000 | |
| Ethanol | 20.0000 | 5.0000 | 10.0000 | 15.0000 | |
| Tetrasodium Glutamate Diacetate | 0.1000 | 0.1000 | 0.1000 | 0.1000 | 0.2000 |
| Sodium Benzoate | 0.5000 | 0.5000 | 0.5000 | 0.5000 | 0.4000 |
| Lactic Acid | 0.0881 | 0.0881 | 0.0881 | 0.0881 | |
| Sodium Lactate | 0.0150 | 0.0150 | 0.0150 | 0.0150 | |
| Sodium Bicarbonate | 0.0010 | 0.0010 | 0.0010 | 0.0010 | 0.0010 |
| Polysorbate 20 | 0.5000 | 0.5000 | 0.5000 | 0.5000 | |
| Phenoxyethanol | 0.7000 | 0.7000 | 0.7000 | 0.7000 | |
| Coco Glucoside, GlyerylOleate (Lamesoft PO65) | 0.0100 | 0.0100 | 0.0100 | 0.0100 | |
| Fragrance | 0.2000 | 0.2000 | 0.2000 | 0.2000 | 0.2000 |
| Caprylic/Capric Triglyceride | 0.0100 | 0.0100 | 0.0100 | 0.0100 | |
| Aloe Barbadensis Leaf Extract | 0.0010 | 0.0010 | 0.0010 | 0.0010 | |
| Tocopheryl Acetate | 0.0010 | 0.0010 | 0.0010 | 0.0010 | 0.0005 |
| Decyl Glucoside | | | | | 0.0010 |
| Sodium Citrate | | | | | 0.1200 |
| Citric Acid | | | | | 0.2300 |
| Gluconic Acid, 50% | | | | | 1.0000 |
| Cucumber Extract | | | | | 0.0010 |
| Aloe, Calendula, Chamomile, Licorice Extract Blend | | | | | 0.0010 |
| Total | 100.0000 | 100.000 | 100.0000 | 100.0000 | 100.0000 |
| Tensile strength* | Pass | Pass | Pass | Pass | Fail |
| Machine Direction average | 707 | 538 | 673 | 797 | 34 |
| Cross Direction average | 695 | 510 | 685 | 764 | 32 |

These and other advantages of the present invention will be apparent to those skilled in the art from the foregoing specification. Accordingly, it is to be recognized by those skilled in the art that changes or modifications may be made to the above-described embodiments without departing from the broad inventive concepts of the invention. It is to be understood that this invention is not limited to the particular embodiments described herein, but is intended to include all changes and modifications that are within the scope and spirit of the invention.

What is claimed is:

1. A moist wipe comprising:
   a. a homogeneous fibrous material comprising one or more cellulosic fibers at about 50 to about 99% w/w and one or more water soluble binders; and
   b. a liquid component comprising
      i. about 74% w/w of water,
      ii. about 15% w/w of dipropylene glycol,
      iii. about 5% w/w of glycereth 26, and
      iv. about 4% w/w of calcium chloride.

2. The moist wipe of claim 1, wherein the liquid component further comprises a chelating agent, an emulsifier, an emollient, a humectant, a pH adjusting agent and an odor neutralizing agent.

3. The moist wipe of claim 1, wherein the liquid component further comprises a fragrance.

4. The moist wipe of claim 1, wherein the liquid component further comprises magnesium aluminum silicate, xanthan gum, cornstarch, silica, and any combination thereof.

5. The moist wipe of claim 1, wherein the moist wipe exhibits a machine direction wet tensile strength greater or equal to about 150 g/inch and a cross direction wet tensile strength of greater than about 75 g/inch.

6. The moist wipe of claim 5, wherein the machine direction wet tensile strength is reduced to less than or equal to about 50 g/in and the cross direction wet tensile strength is reduced to less than or equal to about 25 g/in, after being soaked in water for any duration of time.

7. The moist wipe, of claim 5, wherein the machine direction wet tensile strength and the cross direction wet tensile strength are reduced such that they are no longer measurable after being soaked in water for any duration of time.

8. The moist wipe of claim 5, wherein the moist wipe has a dispersion rate of greater than or equal to about 90% after a time of about 10 seconds when measured according to INDA's Fourth Edition Flushability Guideline Document FG502.R1(18) slosh box disintegration test.

9. The moist wipe of claim 5, wherein the moist wipe has a dispersion rate of greater than or equal to about 70% after a time of about 1 minute when measured according to INDA's Fourth Edition Flushability Guideline Document FG502.R1(18) slosh box disintegration test.

10. The moist wipe of claim 5, wherein the moist wipe has a dispersion rate of greater than or equal to about 50% after a time of about 2 minutes when measured according to INDA's Fourth Edition Flushability Guideline Document FG502.R1(18) slosh box disintegration test.

11. The moist wipe of claim 5, wherein the moist wipe has a dispersion rate of greater than or equal to about 30% after a time of about 5 minutes when measured according to INDA's Fourth Edition Flushability Guideline Document FG502.R1(18) slosh box disintegration test.

12. The moist wipe of claim 1, wherein the moist wipe loses all tensile strength in both the machine and cross directions, when flushed in a toilet, and that falls into small pieces less than ½ in$^2$ with the turbulence of a single flush of a standard household toilet as it goes through the toilet hole to be transferred to household pump basin, not creating any clogs in the household pump or leaving any full wipes intact remaining in the basin, when tested according to the household pump test described in INDA's Fourth Edition Flushability Guideline Document FG503.R1(18) Household Pump Test.

13. The moist wipe of claim 1, wherein the moist wipe exhibits less than about 50 g/in machine direction tensile strength and less than about 25 g/in cross direction tensile strength when soaked in water to go through a municipal pump that falls apart into pieces equal to or less than ½ in$^2$ creating less than 2% or no power increase when tested according to the INDA's Fourth Edition Flushability Guideline Document FG507.R1(18) Municipal Sewage Pump Test.

14. The moist wipe of claim 1, wherein the moist wipe exhibits no measurable strength when soaked in water to go through a municipal pump that falls apart into pieces equal to or less than ½ in$^2$ creating less than 2% or no power increase when tested according to INDA's Fourth Edition Flushability Guideline Document FG507.R1(18) Municipal Sewage Pump Test.

15. The moist wipe of claim 1, wherein the moist t wipe is packaged.

16. The moist wipe of claim 1, wherein the homogeneity of the fibrous material is visualized via scanning electron microscopy.

17. The moist wipe of claim 1, wherein the one or more cellulosic fibers comprises a pulp fiber or a regenerated cellulose fiber and the one or more water soluble binders comprises carboxymethyl cellulose.

18. The moist wipe of claim 17, wherein the one or more cellulose fibers are present at about 75 to 99% w/w of the total weight of the wipe and the carboxymethyl cellulose is present at about 1 to about 25% w/w of the total weight of the wipe.

* * * * *